(12) United States Patent
Schneider et al.

(10) Patent No.: US 7,179,248 B2
(45) Date of Patent: Feb. 20, 2007

(54) EDGE SEAL FOR ABSORBENT ARTICLE AND METHOD FOR MAKING

(75) Inventors: Uwe Schneider, Rheinbach (DE); Christoph Johann Schmitz, Euskirchen-Stotzheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/312,616

(22) Filed: Dec. 20, 2005

(65) Prior Publication Data
US 2006/0100600 A1 May 11, 2006

Related U.S. Application Data

(63) Continuation of application No. 10/262,459, filed on Oct. 1, 2002, now Pat. No. 7,013,941.

(30) Foreign Application Priority Data
Oct. 1, 2001 (EP) .................................. 01122691

(51) Int. Cl.
*A61F 13/15* (2006.01)
(52) U.S. Cl. ...................... 604/385.25; 604/385.26; 604/385.27; 604/385.28; 604/385.29; 604/385.3
(58) Field of Classification Search .......... 604/385.25, 604/385.26, 385.27, 385.28, 385.29, 385.3
See application file for complete search history.

(56) References Cited

U.S. PATENT DOCUMENTS

| | | |
|---|---|---|
| 3,568,676 A | 3/1971 | Del Guercio |
| 3,860,003 A | 1/1975 | Buell |
| 4,381,781 A | 5/1983 | Sciaraffa et al. |
| 4,515,595 A | 5/1985 | Kievit et al. |
| 4,695,278 A | 9/1987 | Lawson |
| 4,710,189 A | 12/1987 | Lash |
| 4,795,454 A | 1/1989 | Dragoo |
| 4,808,178 A | 2/1989 | Aziz et al. |

(Continued)

FOREIGN PATENT DOCUMENTS

EP  0 844 062 A1  5/1998

(Continued)

OTHER PUBLICATIONS

U.S. Appl. No. 10/262,459, filed Oct. 1, 2002, Schneider et al.

*Primary Examiner*—Jacqueline F. Stephens
(74) *Attorney, Agent, or Firm*—George H. Leal; Laura L. Whitmer; Matthew P. Fitzpatrick (57) ABSTRACT

A disposable diaper comprising a topsheet, a backsheet, and an absorbent core disposed between the topsheet and backsheet. The topsheet and backsheet define a periphery and longitudinal edges, portions of the longitudinal edges define leg openings when the diaper is worn. The diaper has a discrete edge seal folded about and joined to the longitudinal edges at least at the portions defining leg openings when the diaper is worn. An apparatus for affixing a discrete edge seal onto a portion of a longitudinal edge of a continuous web and methods for affixing a discrete edge seal onto a predetermined portion of a longitudinal edge of a continuous web are also provided.

8 Claims, 8 Drawing Sheets

U.S. PATENT DOCUMENTS

| | | |
|---|---|---|
| 4,816,025 A | 3/1989 | Foreman |
| 4,857,067 A | 8/1989 | Wood et al. |
| 4,909,803 A | 3/1990 | Aziz et al. |
| 4,938,753 A | 7/1990 | Van Gompel et al. |
| 5,019,067 A | 5/1991 | Simmons |
| 5,026,364 A | 6/1991 | Robertson |
| 5,151,092 A | 9/1992 | Buell et al. |
| 5,221,274 A | 6/1993 | Buell et al. |
| 5,518,801 A | 5/1996 | Chappell et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,607,537 A | 3/1997 | Johnson et al. |
| 5,607,760 A | 3/1997 | Roe |
| 5,609,587 A | 3/1997 | Roe |
| 5,635,191 A | 6/1997 | Roe et al. |
| 5,643,588 A | 7/1997 | Roe et al. |
| 5,662,638 A | 9/1997 | Johnson et al. |
| 5,669,897 A | 9/1997 | Lavon et al. |
| 5,685,874 A | 11/1997 | Buell et al. |
| 5,797,824 A | 8/1998 | Tracy |
| 5,851,204 A | 12/1998 | Mizutani |
| 5,865,823 A | 2/1999 | Curro |
| 6,010,586 A | 1/2000 | Suprise |
| 6,652,504 B1 * | 11/2003 | Olson et al. ........... 604/385.25 |
| 2003/0088227 A1 | 5/2003 | Schneider et al. |

FOREIGN PATENT DOCUMENTS

| | | |
|---|---|---|
| EP | 1 101 470 A2 | 2/2001 |
| WO | WO 95/16746 | 6/1995 |

\* cited by examiner

EDGE SEAL FOR ABSORBENT ARTICLE AND METHOD FOR MAKING

CROSS REFERENCE TO RELATED APPLICATION

This application is a continuation application of U.S. application Ser. No. 10/262,459 filed Oct. 1, 2002 now U.S. Pat. No. 7,013,941; which was the National Stage of International Application No. PCT/US02/31134 filed Oct. 1, 2002.

FIELD OF THE INVENTION

This invention relates to edge seals on absorbent articles, and more particularly to discrete edge seals, such as, discrete elasticized edge seals on disposable absorbent articles, such as diapers.

BACKGROUND OF THE INVENTION

Infants and other incontinent individuals wear disposable absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art.

A typical absorbent article has a chassis that includes a liquid pervious topsheet, and a liquid impervious backsheet joined to the topsheet. An absorbent core is typically positioned between the topsheet and the backsheet. The chassis has a generally elongated shape, which can be rectangular or hourglass shaped. The long dimension of the chassis defines two opposed edges referred to as the longitudinal edges. A portion of each longitudinal edge defines the leg opening of the diaper when worn.

To better contain body exudates, absorbent articles often have elasticized leg openings, referred to as leg cuffs that are designed to fit snugly about the legs of the wearer. Leg cuffs can be made by simply placing tensioned elastic strands along the longitudinal edges, for example. When contracted the elastic strands form gathers of material. Leg cuffs, as opposed to barrier cuffs that are generally disposed inboard, that is, toward the center of the diaper and away from the longitudinal edges of the diaper chassis, can include a portion of the longitudinal edge of the diaper chassis. This longitudinal edge is often unsightly, that is, it appears as an unfinished edge that may have a rather rough appearance. The appearance is important, as consumer perception of softness and comfort are significant considerations for commercial success in the disposable absorbent article field.

In addition to the appearance of leg cuffs in absorbent articles, leg cuffs are relatively costly. In particular, for elasticized leg cuffs, there is a need for elastic in the portion of the longitudinal edge of the chassis that defines the leg opening. However, due to the nature of commercial production of disposable absorbent garments, it is not feasible to apply discrete segments of a material, such as a patch or a strand of elastic material, to a discrete portion of the diaper chassis. For example, it is very difficult to cut a strand of elastic to a length shorter than the long dimension of the chassis and affix it in a predetermined location on the chassis, all at high speed in a repeating manner. For this reason, leg cuff (as well as barrier cuff) elastics are often applied as continuous strands that extend the entire length of the long dimension of the chassis, generally near the longitudinal edges. However, the extra elastic, beyond the portion of the longitudinal edges that define the leg opening, is non-value-added material content.

Accordingly, it would be desirable to have a disposable absorbent article having a leg cuff that has a finished, comfortable appearance.

Additionally, it would be desirable to have a method for making a leg cuff having a finished appearance in a commercially viable manner.

Further, it would be desirable to have a disposable absorbent article with a leg cuff having a finished appearance, with the finished appearance limited to the portion of the longitudinal edge of the chassis that defines a leg opening when worn.

Finally, it would be desirable to have a commercially-viable method of making a disposable absorbent article with a leg cuff having a finished appearance, with the finished appearance limited to the portion of the longitudinal edge of the chassis that defines a leg opening when worn.

BRIEF SUMMARY OF THE INVENTION

In accordance with a first aspect of the present invention, a disposable diaper is provided. The disposable diaper comprises a topsheet, a backsheet, and an absorbent core disposed between the topsheet and the backsheet, the topsheet and the backsheet defining a periphery and longitudinal edges, portions of the longitudinal edges defining leg openings when the disposable diaper is worn, the disposable diaper comprising on each longitudinal edge a discrete edge seal folded about and joined to the longitudinal edges at least at the portions of the longitudinal edges defining leg openings when the disposable diaper is worn, wherein the discrete edge seals do not extend the entire length of the longitudinal edge of the disposable diaper.

In accordance with a second aspect of the present invention, apparatus for affixing a discrete edge seal onto a portion of a longitudinal edge of a continuous web is provided. The apparatus having an axis of rotation, and comprises a) a first web surface disposed at a first radial distance from the axis;

b) an edge seal folder comprising a second web surface disposed at a second radial distance from the axis, the second radial distance being variable between a first minimum distance and a second maximum distance, wherein at the second maximum distance the second radial distance is substantially equal to the first radial distance;

c) the edge seal folder adapted to receive edge seal material on the second web surface at the first minimum distance and to fold and affix the edge seal material as a discrete edge seal onto a portion of the longitudinal edge of the continuous web at the second maximum distance.

In accordance with a third aspect of the present invention, a method of affixing a discrete edge seal onto a predetermined portion of a longitudinal edge of a continuous web is provided. The method comprises the steps of:

a) providing the continuous web;

b) providing a continuous web of edge seal material;

c) providing an edge seal folder that is translatable radially outward with respect to an axis of rotation between a first minimum distance and a second maximum distance;

d) receiving a portion of the continuous web of edge seal material upon a surface of the edge seal folder;

e) applying adhesive to either of the portion of the continuous web of edge seal material or the continuous web in a predetermined location;

f) cutting off the portion of the continuous web of edge seal material from the continuous web of edge seal material;

g) retaining the portion from the continuous web of edge seal material upon the surface of the edge seal folder;

h) translating the edge seal folder from the first minimum distance to the second maximum distance;

i) folding the portion of the continuous web of edge seal material about the predetermined portion of the longitudinal edge of the continuous web; and j) joining the portion of the continuous web of edge seal material to the predetermined portion of the longitudinal edge of the continuous web.

All patents, articles, documents, and other materials cited are, in relevant part, incorporated herein by reference; the citation of any document is not to be construed as an admission that it is prior art with respect to the present invention.

All measurements are in SI units, unless otherwise specified.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

As used herein, the term "absorbent article" refers to devices that absorb and contain body exudates, and more specifically, refers to devices that are placed against or in proximity to the body of the wearer to absorb and contain the various exudates discharged from the body. The term "disposable" is used herein to describe absorbent articles that generally are not intended to be laundered or otherwise restored or reused as an absorbent article (i.e., they are intended to be discarded after a single use).

As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) that in turn are affixed to the other element.

As used herein, the term "elastic" or "elastomeric" refers to any material which, upon application of a biasing force, is stretchable, that is, elongatable, at least about 60 percent (i.e., to a stretched, biased length, which is at least about 160 percent of its relaxed unbiased length), and which, will recover at least 55 percent of its elongation upon release of the stretching, elongation force. A hypothetical example would be a one (1.0) cm sample of a material which is elongatable to at least 1.60 cm, and which, upon being elongated to 1.60 cm and released, will recover to a length of not more than 1.27 cm. Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force. Such materials are referred to herein as "highly elastic".

As used herein, the term "nonelastic" refers to any material that does not fall within the definition of "elastic" (or "elastomeric") or "highly elastic" above.

As used herein, the term "extensible" refers to any material that, upon application of a biasing force, is elongatable, at least about 50% without offering a significant resistance force (less than 10 g/cm) or experiencing catastrophic failure. Catastrophic failure includes substantial tearing, fracturing, rupturing, or other failure in tension such that, if tested in a standard tensile tester, the failure would result in a sudden significant reduction in measured tensile force. As used herein, the term "highly extensible" refers to any material which, upon application of a biasing force, is elongatable, at least about 70%, more preferably at least about 100%, and even more preferably about 120% without offering a significant resistance force (less than 10 g/cm) or experiencing catastrophic failure.

A "unitary" absorbent article refers to absorbent articles that are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso, and includes both tape-type diapers (diapers having adhesive tapes, hook and loop fasteners, and the like, that fastened about the waist of the wearer), and pull-on pant-type diapers. The present invention is also applicable to other absorbent articles such as incontinence briefs, incontinence undergarments, absorbent inserts, diaper holders and liners, and the like.

As used herein, the term "discrete edge seal" or "edge seal" refer to a discrete elongate element that wraps about a portion of a longitudinal edge of a diaper, thus "sealing" that portion of the "edge" of the diaper. Edge seals as described herein provide a soft, finished appearance to the portions of the longitudinal edge of a diaper that form the leg openings when worn.

Figure 1:
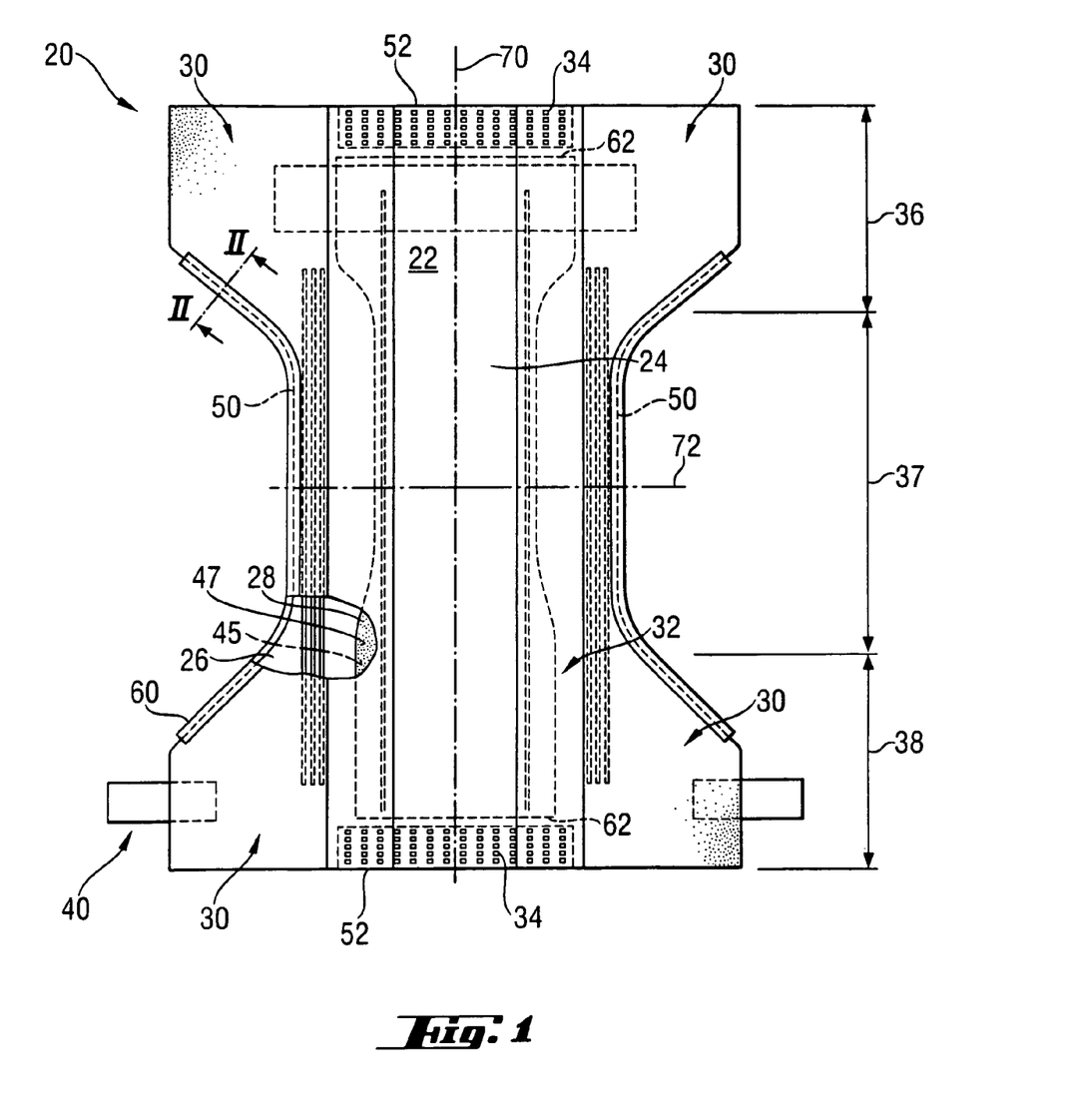
FIG. 1 is a perspective view of one embodiment of an absorbent article of the present invention.

FIG. 1 is a plan view of the diaper 20 of the present invention in a flat-out state with portions of the structure being cut away to more clearly show the construction of the diaper 20. The portion of the diaper 20 that faces the wearer is oriented towards the viewer. As shown in FIG. 1, the diaper 20 preferably comprises a liquid pervious topsheet 24; a liquid impervious backsheet 26, an absorbent core 28 which is preferably positioned between at least a portion of the topsheet 24 and the backsheet 26; side panels 30; elasticized leg cuffs 32; and an elastic waist feature 34.

Diaper 20 is shown in FIG. 1 to have a first waist region 36, a second waist region 38 opposed to the first waist region 36 and a crotch region 37 located between the first waist region and the second waist region 38. The periphery of the diaper 20 is defined by the outer edges of the diaper 20 in which the longitudinal edges 50 are oriented generally parallel to the longitudinal centerline 70 of the diaper 20 and the end edges 52 run between the longitudinal edges 50 generally parallel to the transverse centerline 72 of the diaper 20. However, for better fit, longitudinal edges 50 are preferably curved to produce an "hourglass" shape diaper when viewed in the flat-out configuration of FIG. 1. The chassis 22 of the diaper 20 comprises the main body of the diaper 20. The chassis 22 comprises at least the topsheet 24 and the backsheet 26.

For tape-type diapers, that is, diapers intended to be fastened about the wearer by use of an adhesive tape or releasable mechanical fastener, the diaper 20 can have a fastening system generally designated 40, as is commonly known in the art. Once fastened upon the wearer, portions of longitudinal edge 50 define leg openings. For pant-type diapers, first waist region 36 is joined by suitable means to the second waist region 38, as is commonly known in the art, to make a pant-type garment having leg openings defined by the non-joined portions of longitudinal edges 50. Joining of the waist regions can be by thermal bonding, adhesive bonding, or ultrasonic bonding, for example.

While the topsheet 24, the backsheet 26, and the absorbent core 26 may be assembled in a variety of well-known configurations, preferred tape-diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; and U.S. Pat. No. 5,580,411 entitled "Zero Scrap Method For Manufacturing Side Panels For Absorbent Articles" which issued to Nease et al. on Dec. 3, 1996. Preferred pant-type diapers and methods for making suitable side seams are disclosed in U.S. Pat. No. 5,569,234 issued to Buell, et al. on Oct. 29, 1996, U.S. Pat. No. 5,607,537 issued to Johnson et al. on Mar. 4, 1997, U.S. Pat. No. 5,662,638 issued to Johnson et al. on Sep. 2, 1997, and U.S. Pat. No. 5,685,874 issued to Buell et al. on Nov. 11, 1997. Preferable seams are disclosed in European Patent Application No. 96118654.1 titled "Thermal Joining of Webs" filed on Nov. 21, 1996 (Christoph J. Schmitz).

The backsheet 26 is generally that portion of the diaper 20 positioned adjacent the garment facing surface 45 of the absorbent core 28 which prevents the exudates absorbed and contained therein from soiling articles which may contact the diaper 20, such as bed sheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names XI 5306, X10962 and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and micro porous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL® blend P18–3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. SELF webs suitable for the present invention are more completely described in U.S. Pat. No. 5,518,801 entitled Web Materials Exhibiting Elastic-Like Behavior, which issued to Chappell, et al. on May 21, 1996.

The backsheet 26 may be joined to the topsheet 24, the absorbent core 28 or any other element of the diaper 20 by any attachment means known in the art. For example, hot melt adhesives applied about the portions of the peripheral edges can be sufficient to join the topsheet and backsheet to one another.

The topsheet 24 is preferably positioned adjacent the body surface 47 of the absorbent core 28 and may be joined thereto and/or to the backsheet 26 by any attachment means known in the art. The topsheet 24 is preferably compliant, soft feeling, and non-irritating to the wearer's skin. Further, at least a portion of the topsheet 24 is liquid pervious, permitting liquid to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; melt-blown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The diaper 20 can also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 62 of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24. The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989.

The diaper 20 may also include a fastening system 40. In particular, tape-type diapers have a fastening system. The fastening system 40 preferably maintains the first waist region 36 and the second waist region 38 in an overlapping configuration so as to provide tension about the circumference of the waist opening of the diaper 20 to hold the diaper 20 on the wearer. The fastening system 40 preferably comprises tape tabs and/or hook and loop fastening components, although any fastening means known in the art is generally acceptable.

In pant-type diapers, opposing sides, i.e., longitudinal edge portions of first waist region 36 and second waist region 38, of the garment are seamed or welded to form a pant, as is known in the art. This allows the article to be used as a pull-on type diaper, such as a training pant.

The diaper 20 can also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may be constructed in any suitable configurations as known in the art. Examples of diapers with elasticized side panels are disclosed in U.S. Pat. No. 4,857,067, entitled Disposable Diaper Having Shirred Ears issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled Absorbent Articles Providing Sustained Dynamic Fit; U.S. patent application Ser. No. 08/155,048 entitled Absorbent Article With Multi-Directional Extensible Side Panels filed Nov. 19, 1993 in the names of Robles, et al.

The diaper 20 preferably further includes leg cuffs 32 which provide improved containment of liquids and other body exudates. Leg cuffs may also be referred to as leg-bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) that improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs.

In prior art diapers longitudinal edges 50 were left unfinished, that is, the edges of the component webs, such as the topsheet 24 and backsheet 26, were left exposed. Although functional, this configuration leaves the diaper with an unfinished look. Attempts to make the diaper more garment-like by finishing the longitudinal edges 50 in an economical manner have thus far proved unsatisfactory. Edge folding and seaming, for example, particularly on a curved "hour-glass" shaped edge, requires complex equipment, and, at best, would only slightly improve the appearance of the edge 50. The addition of separate, discrete portions of edge-finishing materials involves the cutting and accurate placement of materials on high-speed equipment, which, until the present invention, has proved impractical as well.

The article of the present invention is an improved diaper having a finished edge cuff. The finished edge cuff comprises an edge seal 60 that is joined to a portion of longitudinal edge 50. Edge seal 60 preferably comprises a soft, pliable, non-irritating nonwoven material, and is discrete. Edge seal can be extensible, and can be elastic or highly elastic, or rendered elastic or highly elastic. In general, materials described as suitable for the topsheet 24 are also suitable materials for use as the edge seal 60. By discrete is meant that the edge seal 60 is not applied as a continuous member to the entire length of longitudinal edge 50 during diaper manufacture, thereby extending the entire longitudinal length of the diaper 20. Therefore, one advantage of the present invention is edge seal 60 need only be joined about longitudinal edge 50 along portions defining the leg opening when diaper 20 is worn. This represents a significant material cost savings. Therefore, each edge seal 60 comprises a discrete edge seal 60 that is joined to the diaper 20 in a folded configuration such that it wraps, or encloses, at least a portion of the longitudinal edge 50 of the diaper 20 to give the leg opening of diaper 20 a finished, seamed, appearance.

Preferably each edge seal 60 has dimensions such that when the diaper 20 is worn, the edge seal 60 completely encircles the portion of longitudinal edge that defines the leg opening.

Accordingly, in one embodiment, the present invention can be described as a disposable diaper (tape-type or pant-type) comprising a topsheet, a backsheet, and an absorbent core disposed between the topsheet and said backsheet, the topsheet and backsheet defining a periphery and longitudinal edges, portions of the longitudinal edges defining leg openings when the diaper is worn, and an edge seal folded about and joined to the longitudinal edges at least at the portions defining leg openings when the diaper is worn. In one embodiment the edge seals are joined about the longitudinal edges only at the portions defining the leg openings. In one embodiment the edge seals do not extend the entire length of the longitudinal edge of the diaper.

Figure 2:
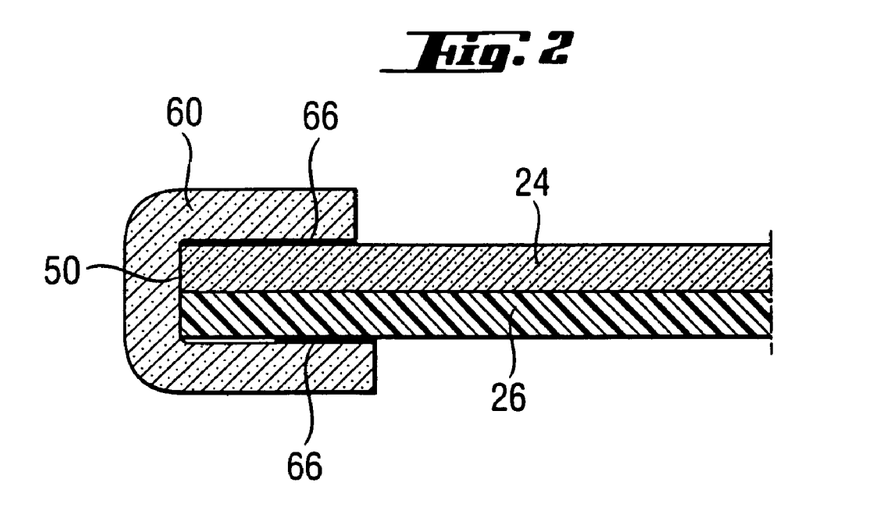
FIG. 2 is a cross-sectional view of a portion of an edge seal portion of the absorbent article shown in FIG. 1.

The fold of the edge seal 60 about the edge of the diaper can be described as a C-fold, or an "edge wrap" and one embodiment is shown more clearly in the cross sectional view of FIG. 2. As shown in FIG. 2, edge seal 60 wraps completely around longitudinal edge 50, such that longitudinal edge 50 is no longer exposed at the edge-sealed portions. Edge seal 60 can be joined in ways known in the art for bonding nonwoven webs, such as by adhesive bonding. For example, hot melt adhesive 66 can be applied to portions of topsheet 24, backsheet 26, and/or edge seal 60 prior to placement of edge seal 60 in the folded configuration about longitudinal edge 50. If necessary, heat and pressure can be applied as well to ensure sufficient joining of the edge seal 60.

Edge seal 60 can be longitudinally elastic. That is, in one embodiment, edge seal 60 comprises an elastomeric material and edge seal 60 is affixed to longitudinal edge 50 while in a stretched, elongated condition. Once tension is released from edge seal 60, it can then contract longitudinally to form gathers along the leg opening of the diaper. The gathers give the diaper leg opening a soft, plush look and feel. Elastomeric properties can be achieved by the use of an elastomeric nonwoven material for example, or by the addition of elastic strands to edge seal 60.

Figure 3:
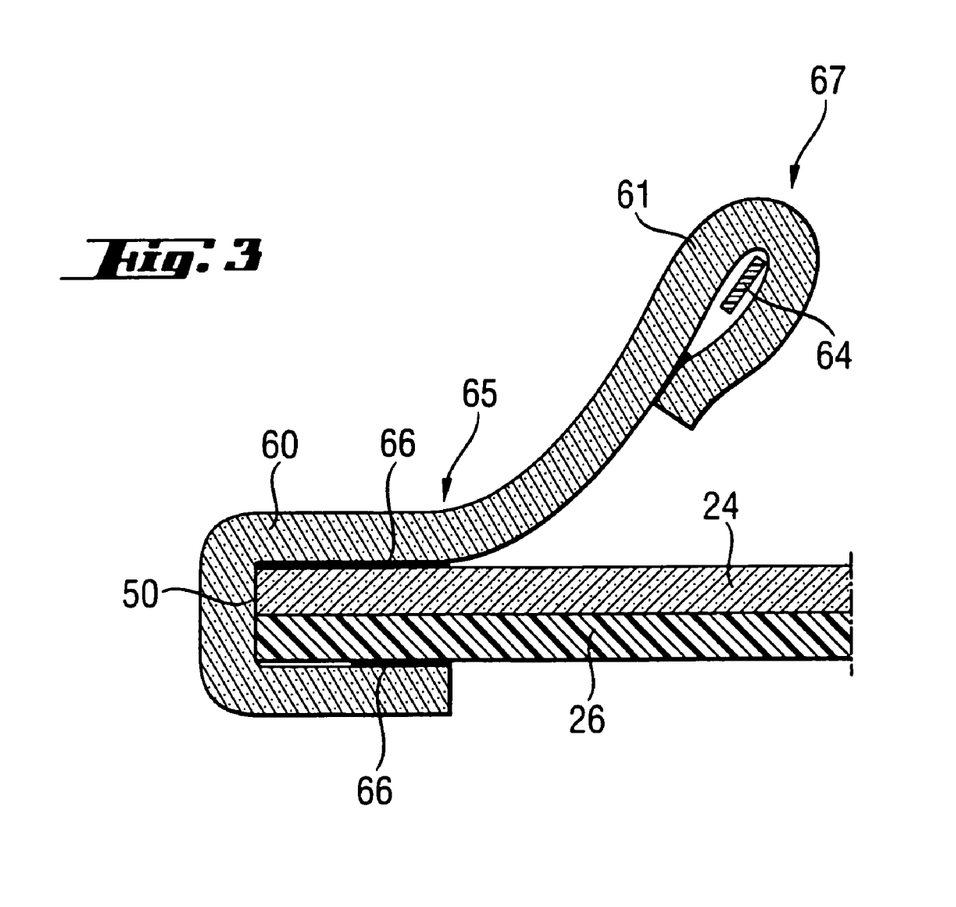
FIG. 3 is a cross-sectional view of an alternative embodiment of an edge seal portion of an absorbent article.

As shown in FIG. 3, a portion of edge seal 60 can be extended to form an integrated barrier cuff portion 61, which can replace, or complement elasticized leg cuffs 32. Barrier cuff portion 61 is joined to edge seal 60 at a proximal portion 65, and overlaps topsheet 24, but is unattached to topsheet 24 at a distal portion 67. In a preferred embodiment, distal portion 67 comprises an elastic component such as elastic strand 64, or other elastic components as are known in the art of elasticized leg cuffs including barrier leg cuffs. Thus, when in use, elasticized distal portion 67 can "stand up" to form a barrier cuff, as is known in the art of barrier cuffs.

Apparatus and Method of Making

The edge seals 60 can be affixed to the absorbent article by hand, such as by gluing in position while the article is in a flat, extended configuration. However, such a process is time and labor intensive, and is not feasible for commercial production of absorbent articles. Therefore, the apparatus and method disclosed herein is preferred for commercially viable production of absorbent articles having an edge seal 60, and in particular a discrete edge seal 60 (i.e., an edge seal 60 that not extend the entire length of the longitudinal edge 50 of the diaper).

Figure 4:
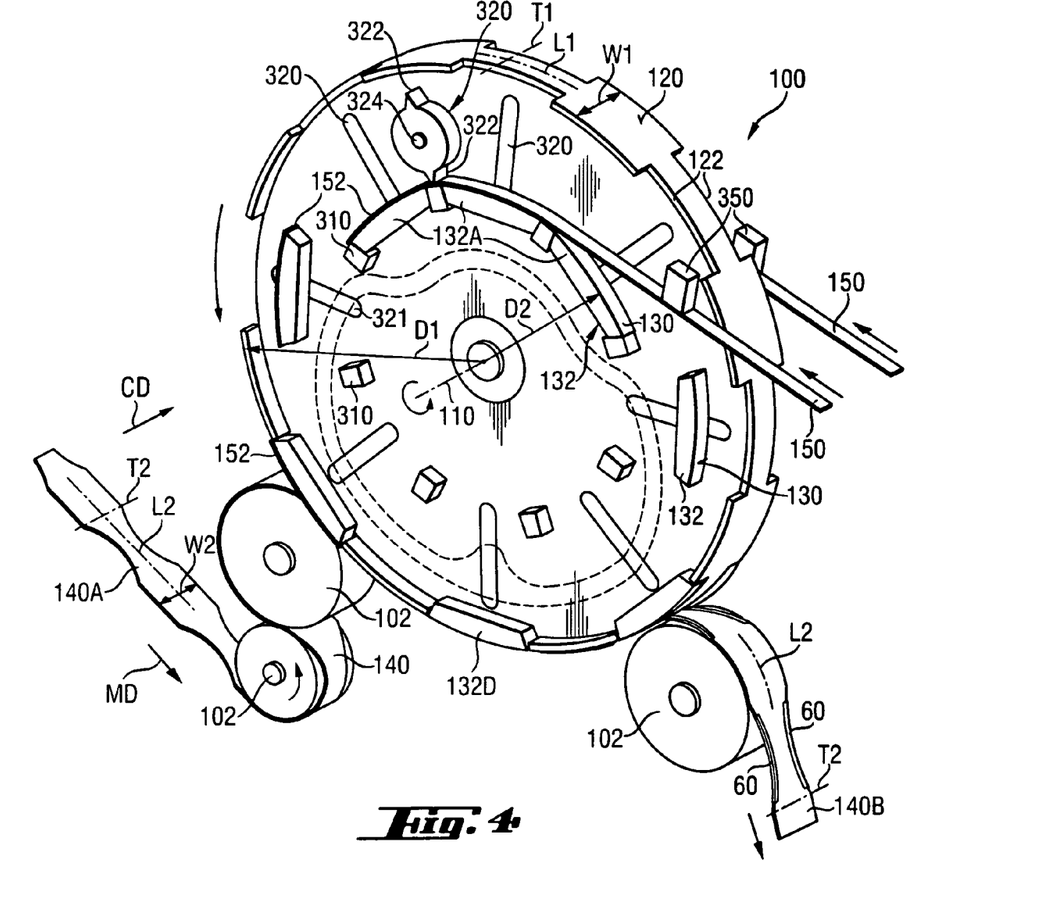
FIG. 4 is a perspective schematic representation of an apparatus of the present invention for making an absorbent article of the present invention.

FIG. 4 shows a schematic representation of an apparatus 100 for making an absorbent article having an edge seal 60. To process absorbent articles in a commercially viable manner, the apparatus is designed to process materials supplied from continuous webs. However, since in a preferred embodiment the edge seal 60 is affixed as a discrete edge seal segment (i.e., not a continuous web), the apparatus 100 is designed to process an edge seal web material supplied from a continuous web to produce a discrete edge seal 60 affixed at spaced apart locations to portions of the longitudinal edge of a continuous web of material that eventually will comprise the chassis of a diaper.

In a commercially viable embodiment edge seals 60 are affixed to both longitudinal edges 50 of diaper 20 simultaneously. Therefore, although the apparatus and process are described below with respect to one edge seal web 150 forming one edge seal 60, it should be appreciated that the apparatus 100 preferably is configured substantially symmetrically, such that two continuous edge seal webs 150 are simultaneously supplied to and processed by the apparatus 100 shown in FIG. 4. Therefore, the description of the apparatus with respect to FIG. 4, for example, is directed to the operation of the apparatus with respect to the side of the apparatus visible in FIG. 4. But the apparatus 100 is two-sided, such that both webs 150 shown in FIG. 4 are simultaneously processed into edge seals 60 of the finished article.

To accomplish the task of applying edge seal 60 in a spaced relationship to a continuous web of material being processed at high speed, the apparatus 100 is a rotary apparatus wherein certain operative surfaces rotate about a common axis 110 in a continuous, repeating process, as described herein. In general, the apparatus 100 works on the principle of differential surface path lengths of circumferential (or peripheral) surfaces. That is, as the radial distance from the axis 110 increases, the circumference of a circle associated with the radial distance also increases. The apparatus 100 has at least two operative surfaces, referred to a "web surfaces" herein because the surfaces are designed to handle web materials in a continuous cyclic process.

A first web surface 120 is disposed at a first radial distance D1 from axis 110. The distance D1 can be, as shown in FIG. 4, a fixed distance (i.e., first web surface 120 defines a circular configuration when viewed in profile, that is, parallel to axis 110), but can be a variable distance (i.e., first web surface 120 defines a polygonal configuration when viewed in profile, that is, parallel to axis 110). First web surface 120 is preferably continuous, such as the circumferential surface of a right circular cylinder (D1 is fixed and constant) or the peripheral surface of a right polygonal cylinder (D1 varies from a minimum measured to the center of each polygonal segment to a maximum at the vertex of the angle formed by adjacent polygonal segments). Regardless of the particular configuration of first web surface 120, in a preferred embodiment any given point on first web surface 120 remains at a constant distance D1 from axis 110 during the operation of apparatus 100.

First web surface 120 has a longitudinal axis L1 and a transverse axis T1 perpendicular to longitudinal axis L1. First web surface 120 also has a width W1 measured parallel to the transverse axis T1. Width W1 can be constant or varying.

A portion of first web surface 120 supports a continuous web 140 having a longitudinal axis L2 oriented in the machine direction MD, and a transverse axis T2 perpendicular to longitudinal axis L2. Continuous web 140 also has a width W2 measured in the cross-direction CD, parallel to the transverse axis T2 (perpendicular to the MD), and width W2 can be constant or varying. In operation, continuous web 140 can be guided adjacent to, and preferably in contact with, a portion of first web surface 120, which is designed to support web 140 during the portion of the process in which portions of edge seal web material 150 are folded and joined thereto to become edge seals 60 as discussed more fully below. In a preferred embodiment, during processing as described herein, the longitudinal axis L2 of web 140 is aligned parallel and adjacent to longitudinal axis L1 of first web surface 120.

Continuous web 140 can be a portion of the absorbent article in process. That is, continuous web 140 can be a laminate web comprising multiple layers of component materials, such as diaper chassis materials, in the process of being assembled into a finished absorbent article, as is known in the art of commercial disposable diaper manufacture. For example, continuous web 140 can be a liquid impermeable backsheet material, or a nonwoven topsheet material. In a preferred embodiment, continuous web 140 is a laminate comprising a continuous web of backsheet and topsheet material joined together as is known in the art of diaper manufacture. In a preferred embodiment, as shown on incoming continuous web 140A in FIG. 4, portions of longitudinal edges of continuous web 140 are cut, or "notched" to form curvilinear notched portions that form an "hourglass" shaped chassis in the finished article. A plurality of discontinuous and spaced apart absorbent core elements (not shown in FIG. 4) can be disposed between the continuous web of backsheet and topsheet materials.

Continuous web 140 can be guided adjacent to web surface 120 by any suitable means. In one embodiment, as shown in FIG. 4, guide rollers 102 are operatively positioned such that continuous web 140 is urged against a portion of web surface 120, which correspondingly supports continuous web 140 for a portion that can be described as a defined arc length of first web surface 120. If first web surface 120 is not at a constant distance from axis 110, i.e., the web surface 120 is not circular in shape when viewed parallel to axis 110, then guide rollers 102 can be correspondingly operatively positioned. For example, in one embodiment, each guide roller 102 can itself be spaced a distance from axis 110 equal to or greater than the maximum distance D1. In another embodiment guide rollers 102 can be biased, such as by spring loading, to provide constant pressure against web surface 120 even as its radial distance from axis 110 changes.

In operation, continuous web 140 is guided in the direction shown by the arrows associated therewith, as the apparatus 100 rotates about axis 110 in the direction shown by the arrows associated therewith (counter-clockwise as viewed in FIG. 4). The linear, i.e., tangential speed of web surface 120 is essentially the same as, and preferably exactly the same as, the linear speed of continuous web 140, such that during the portion of the process in which continuous web 140 is disposed adjacent first web surface 120, there is no relative motion between continuous web 140 and first web surface 120.

In one embodiment, first web surface 120 can have a varying width W1 defining spaced apart notches 122. In a preferred embodiment, the varying width W1 defines a plurality of regularly spaced, opposing notches, as shown in FIG. 4. In operation of a preferred embodiment of apparatus 100 the notches correspond to corresponding notched portions of continuous web 140 to which edge seals 60 are applied. That is, notched portions of continuous web 140 line up adjacent to respective notched portions of first web surface 120 when continuous web 140 is disposed adjacent to first web surface 120. Thus, edge seals 60 can be discrete members that provide a finished edge to the leg openings defined by the concave portions of an hourglass-shaped diaper chassis. However, it is not necessary that first web surface 120 exhibit such notches. In one embodiment of apparatus 100, for example, portions of the width W2 of web 140 are sufficiently greater than a constant width W1 of web surface 120, so that the edge seals 60 can be affixed to such portions (i.e., overhanging edges of web 140).

Edge seals 60 are discrete elements joined to a portion of each longitudinal edge 50 of diaper 20. However, in a commercially viable process, it is necessary that edge seals 60 be processed from a continuous web material preferably supplied as roll stock or festooned for substantially continuous processing as a web. To facilitate web joining of a relatively short discrete member to a relatively longer continuous member, the apparatus 100 of the present invention has a second web surface 130 that is at a second radial distance D2 from axis 110. Second web surface 130 can be comprised of a plurality of edge seal folders 132, each of which are preferably identical to one another. Each edge seal folder 132 is designed to convey a discrete edge seal portion 152, which, once folded and joined to continuous web 140 becomes edge seal 60. Thus, edge seal folders 132 receive a continuous web of edge seal material 150 and subsequently facilitate control of edge seal material 150 as it is cut to make a discrete edge seal portion 152 having a predetermined length and which is translated to a predetermined position and folded and joined about a predetermined portion of continuous web 140 to form an edge seal 60 of the present invention. The predetermined locations are spaced apart, and correspond to the portion of the chassis longitudinal edges 50 that define at least portions of a leg opening when the finished garment is worn.

Each edge seal folder 132 defines a portion of second web surface 130 that can be substantially flat in profile (i.e., as viewed parallel to axis 110), or each can define a second web surface 130 that makes an arc segment in profile as shown in FIG. 4. The actual profile of edge seal folders 132 preferably matches the profile of first web surface 120. That is, the arc radius defined by the second web surface 130 of edge seal folders 132 is preferably identical to the arc radius defined by the first web surface 120.

Figure 5:
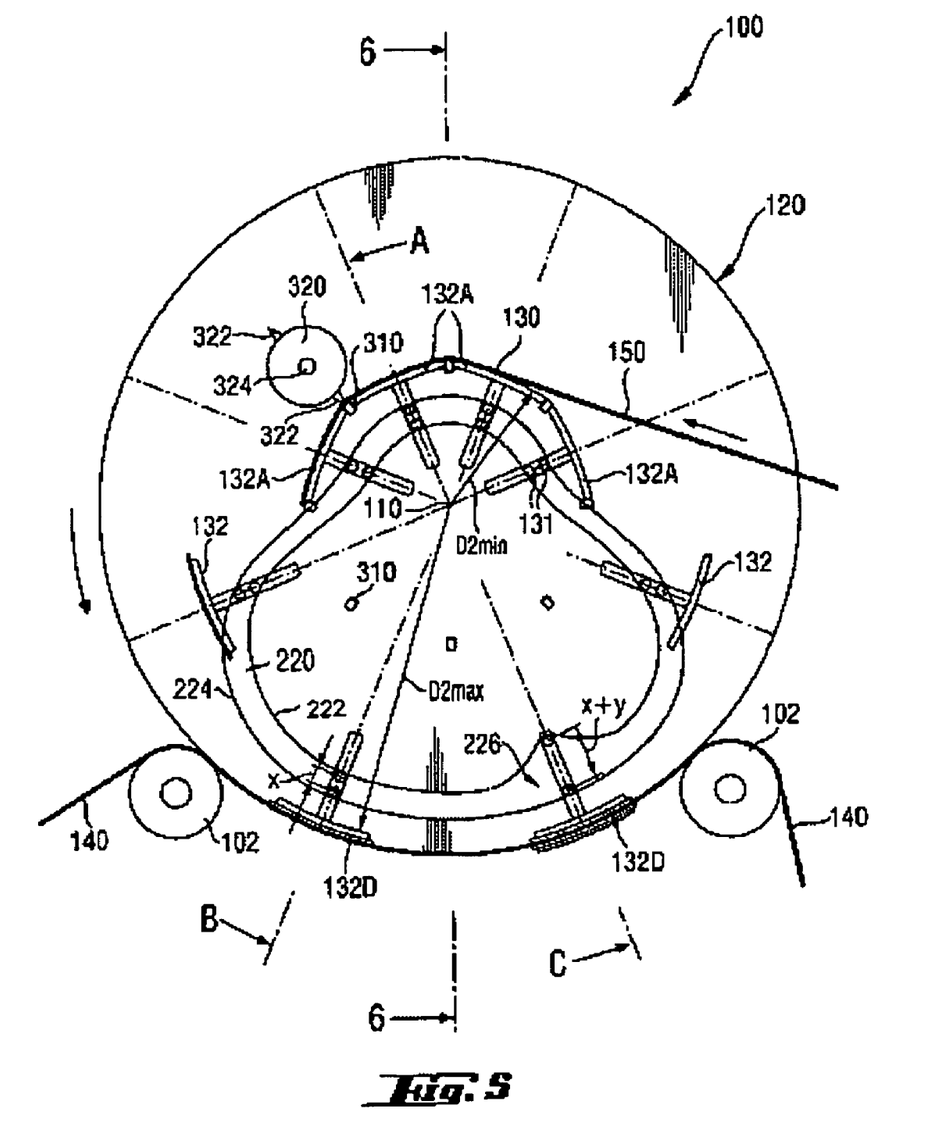
FIG. 5 is a schematic representation of an apparatus of the present invention for making an absorbent article of the present invention.

Each edge seal folder 132 occupies a position at a variable distance D2 from axis 110. Each edge seal folder 132 can translate, i.e., move, from a first position that is a minimum radial distance D2$min$ from axis 110 to a second position that is a maximum radial distance D2$max$ from axis 110, as shown in FIG. 4. Three edge seal folders 132 shown as segments 132A in FIGS. 4 and 5 are at minimum radial distance D2$min$. In the embodiment shown in FIG. 4, the apparatus 100 rotates as shown by the arrow associated therewith (i.e., in a counter-clockwise manner as viewed in FIG. 4), and as it rotates, edge seal folders 132 are translated from minimum radial distance D2min in a direction away from axis 110 until they reach a maximum radial distance D2max. An edge seal folder 132 in this position is shown as segment 132D in FIGS. 4 and 5.

In addition to translating in a direction radially outwardly from (or inwardly toward) axis 110, edge seal folders 132 preferably translate in a direction parallel to axis 110. That is, as can be seen best in the cross section of FIG. 6, edge seal folders 132 receive continuous edge seal web 150 at a maximum distance from line of symmetry 112, and move toward the line of symmetry 112 when moving away from axis 110. In this manner, both continuous webs 140 and 150 can be processed from their respective supply packages generally to one another.

In the embodiment shown in FIG. 4, when segments 132 are at the maximum radial distance D2$max$, the second web surface 130 and first web surface 120 are at a substantially equal radial distance from axis 110. By "substantially equal" is meant that, for practical purposes, the two surfaces are the same distance from axis 110, but the term is not meant to convey mathematical exact equality. In some processes it may be desirable to have a difference in radial distance between the first and second web surfaces when a edge seal folders 132 are at the maximum radial distance D2max.

Edge seal folders 132 are translated from a first position, at which position edge seal web 150 is operatively disposed thereon, to a second position, at which position the edge seal portion 152 is folded and affixed to the continuous web 140, that is, to what will eventually be the longitudinal edges of a disposable diaper, and back to the first position in a continuous, repeating process. By "operatively disposed" thereon is meant that the edge seal web 150 is received by and disposed on edge seal folder 132 in a generally flattened, extended position and orientation with respect to the edge seal folder 132, such that once edge seal web 150 is cut into discrete edge seal portion 152 and edge seal folder 132 begins translating it to its respective second position, the edge seal portion 152 is accurately positioned for folding and affixing to the continuous web 140 to form a completed edge seal 60.

Figure 6:
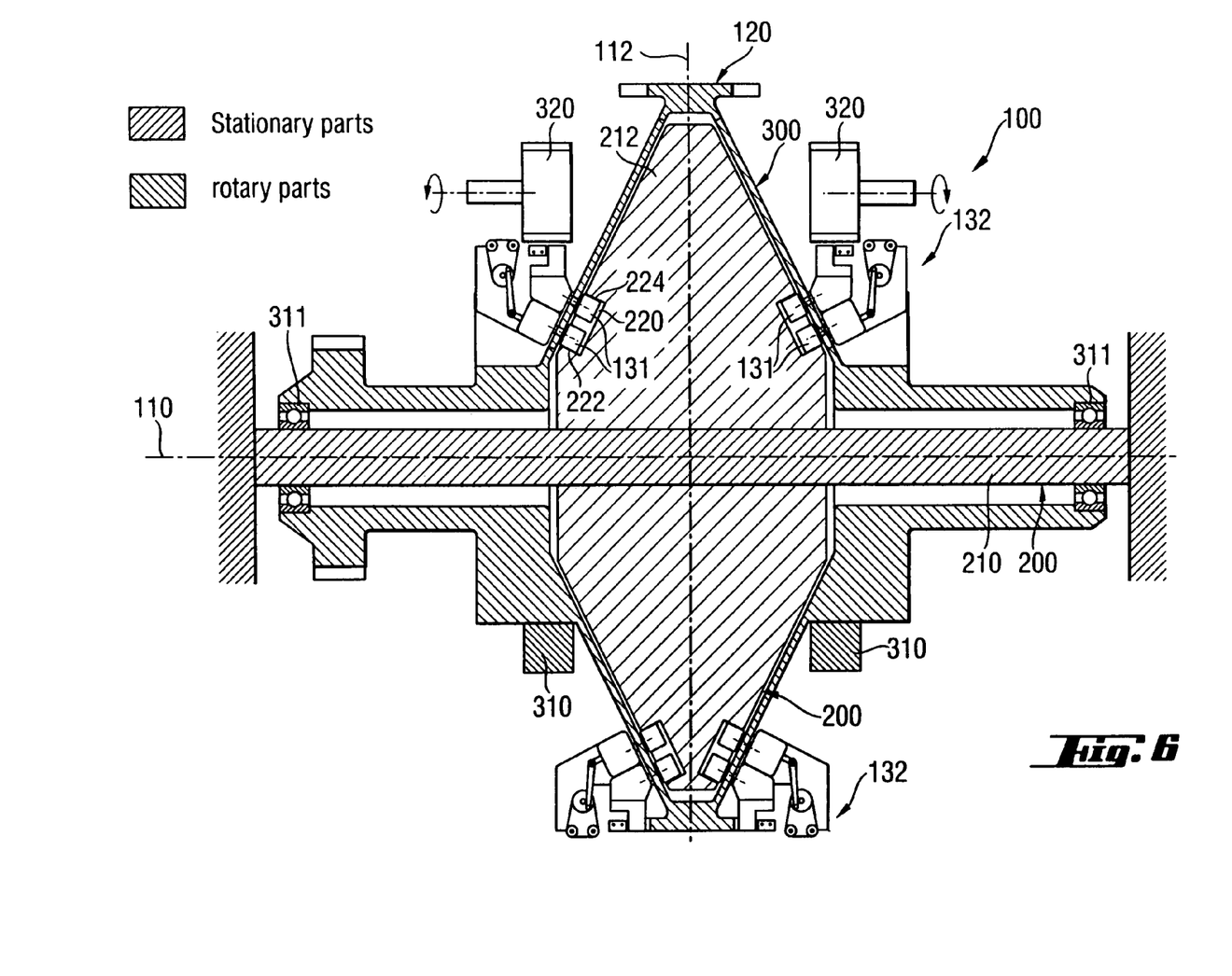
FIG. 6 is a schematic cross-sectional view of an apparatus of the present invention.

The apparatus and process are now discussed in more detail with reference to a particular method of operation with respect to FIGS. 4, 5 and 6. FIG. 5 is a schematic representation of the apparatus 100 as viewed parallel to axis 110. FIG. 6 is a cross-sectional view of apparatus 100.

As one can see with reference to FIGS. 4 and 5, the apparatus 100 permits continuous webs 140, 150 to be processed into an article of the present invention having discrete (i.e., non-continuously applied) edge seals 60. That is, although each edge seal could be supplied as discrete "patches" or sheets of material, and applied by hand or by automatic placement equipment onto the second web surface 130 of each edge seal folder 132 when it is at its first position D2min, in a preferred embodiment, edge seal web material 150 is supplied as a continuous web of material, such as a relatively narrow strip of nonwoven material. While the general principle of operation can be practiced in various ways, the following description is intended to be a nonlimiting example of a currently preferred apparatus.

Apparatus 100 comprises a stationary portion 200 and a rotating portion 300. Stationary portion 200 comprises a mounting shaft 210 that is parallel to, and coaxial with axis 110 of apparatus 100. Affixed to shaft 210 is cam plate 212. Cam plate 212 comprises a cam track 220, which itself comprises an inner cam track surface 222 and an outer cam track surface 224. Rotating portion 300 can be mounted on suitable bearings 310, such as ball bearings, and rotates about shaft 210. First surface 120 forms an outer periphery of rotating portion 300. Rotating portion 300 has a plurality of slots 320 (shown in FIG. 4) and guides 330 (shown in FIG. 7) that serve to facilitate linear motion of edge seal folders 132 in a direction radially outwardly from axis 110. Guides 330 can be linear slide bearings, for example. Each edge seal folder 132 is operatively attached through a respective slot 320 to a pair of cam followers 131 disposed in operative relationship within cam track 220. Therefore, as rotating portion 300 is rotated, each edge seal folder 132 is forced by the cam followers 131 in cam track 220 to follow a complex path, rotationally about and away from axis 110 and toward plane of symmetry 112, or vice-versa, depending on where the edge seal folder is in the cycle of operation. Starting from the position identified as 132A, the rotation of rotating portion 300 forces edge seal folders 132 to translate relative to axis 110, which has the effect of moving portions of second web surface 130 from minimum distance D2min to maximum distance D2max with respect to axis 110 and back in a repeating cycle.

In a preferred embodiment of apparatus 100, when at minimum distance D2min, each edge seal folder 132 is separated from adjacent edge seal folders 132 by a stationary anvil 310 that provides a cutting surface for a web cutting device, such as rotary knife 320. Stationary anvil 310 is stationary with respect to rotating portion 300, and can be, for example, a permanently affixed (to rotating portion 300), relatively rigid member having a relatively smooth cutting surface.

Rotary knife 320, mounted separately from rotating portion 300, can have a plurality of cutting blades 322 that operate in timed sequence with rotary portion 300 such that cutting blades 322 sever edge seal web material 150 thereby forming discrete edge seal portions 152. Other cutting methods can be utilized, such as laser cutting, high-speed fluid cutting, saw blade cutting, and the like. In the embodiment shown in FIGS. 4 and 5, rotary knife 320 is rotatable upon its axis of rotation 324, which is parallel to axis 110 of apparatus 100. The rotary knife 320 rotates in a timed relationship with rotary portion 300, such that the blade cuts continuous web 150 at a location corresponding to an area between adjacent edge seals folders 132, while the respective adjacent edge seal folders are each at the position designated as 132A.

In another embodiment, web 150 can be perforated across its width in a regularly repeating pattern of spaced apart, longitudinally extending perforations (e.g., as is common in rolled toilet tissue). In this configuration, the distance between lines of perforation would correspond to the long dimension of edge seal folder 132. As each edge seal folder 132 begins translating from the first position D2min to the second position, D2max, the lines of perforation can tear, thereby rendering each edge seal portion 152 discrete and operatively disposed on its respective edge seal folder 132.

In operation, therefore, as rotating portion 300 rotates edge seal web material 150 is drawn onto second web surface 130 while second web surface is at minimum distance D2min. In FIG. 5, edge seal folders 132 designated 132A are shown in the position in which edge seal web material 150 is drawn or received onto apparatus 100 as rotating portion 300 rotates about axis 110. To stabilize edge seal web material 150 in position on second web surface 130, each edge seal folder 132 can have vacuum ports to which a partial pressure is applied. In this manner, edge seal web material 150 is held in position on each edge seal folder by vacuum, or suction, forces. The back tension applied to edge seal web material 150 as it is drawn from its supply package (e.g., roll or festoon), is controlled in conjunction with the forces supplied by the vacuum on edge seal folders 132 to ensure edge seal web material 150 is drawn onto apparatus 100 in a stable, continuous process. Vacuum can be applied in ways known in the art, such as by suitable arrangements of pumps, tubes, and vacuum ports. Other means known in the art for stabilizing web materials can be used as well. For example, each edge seal folder can have a light-tack adhesive applied to the surface 130 such that edge seal web material 150 is removably adhered in place when cut into edge seal portions 152.

After having been cut by rotary knife 320, discrete edge seal portion 152 is disposed on its respective edge seal folder 132 in a generally flattened (i.e., unfolded) position. Following the sequence of motion counter-clockwise (with respect to FIG. 5), the edge seal folder 132 is translated via the interaction of cam followers 131 and cam track 220 outwardly with respect to axis 110 and inwardly with respect to plane of symmetry 112 toward first web surface 120. At its maximum distance from axis 110, which is D2max, second web surface 130 is at a distance from axis 110 that is essentially equal to that of first web surface 120. At this position, edge seal web portion 152 is adjacent to and partially overlaps continuous web 140.

Edge seal portion 152 is folded upon a longitudinal edge of continuous web 140 to form edge seal 60 by a folding action of edge seal folders 132. Edge seal folders 132 can be formed of two independent halves, for example, such that one half can fold over onto the other half, thereby making the C-fold of the edge seal portion 152, which can be joined in a folded condition onto continuous web 140 as edge seal 60 of the finished diaper. The folding action can be achieved by methods known in the art, for example by way of flexible hinged elements operated by mechanical linkage. The folding can be accomplished via belt driven linkages, hydraulic linkages, servo motors, and the like, actuated in timed sequence with the rotary cycle of apparatus 100.

In a preferred embodiment, the folding action is achieved by linkage controlled by the cam followers 131 of each edge seal folder 132 when in a predetermined position relative to the rotating cycle of apparatus 100. This arrangement provides positive timing control to the folding step. In a preferred embodiment, a pair of cam followers 131 is associated with each edge seal folder 132, with the two cam followers independently moveable. In a preferred embodiment each such cam follower 131 is biased against either the inner cam track surface 222 or the outer cam track surface 224. Biasing can be accomplished by means known in the art, such as by spring loading, for example.

Figure 8:
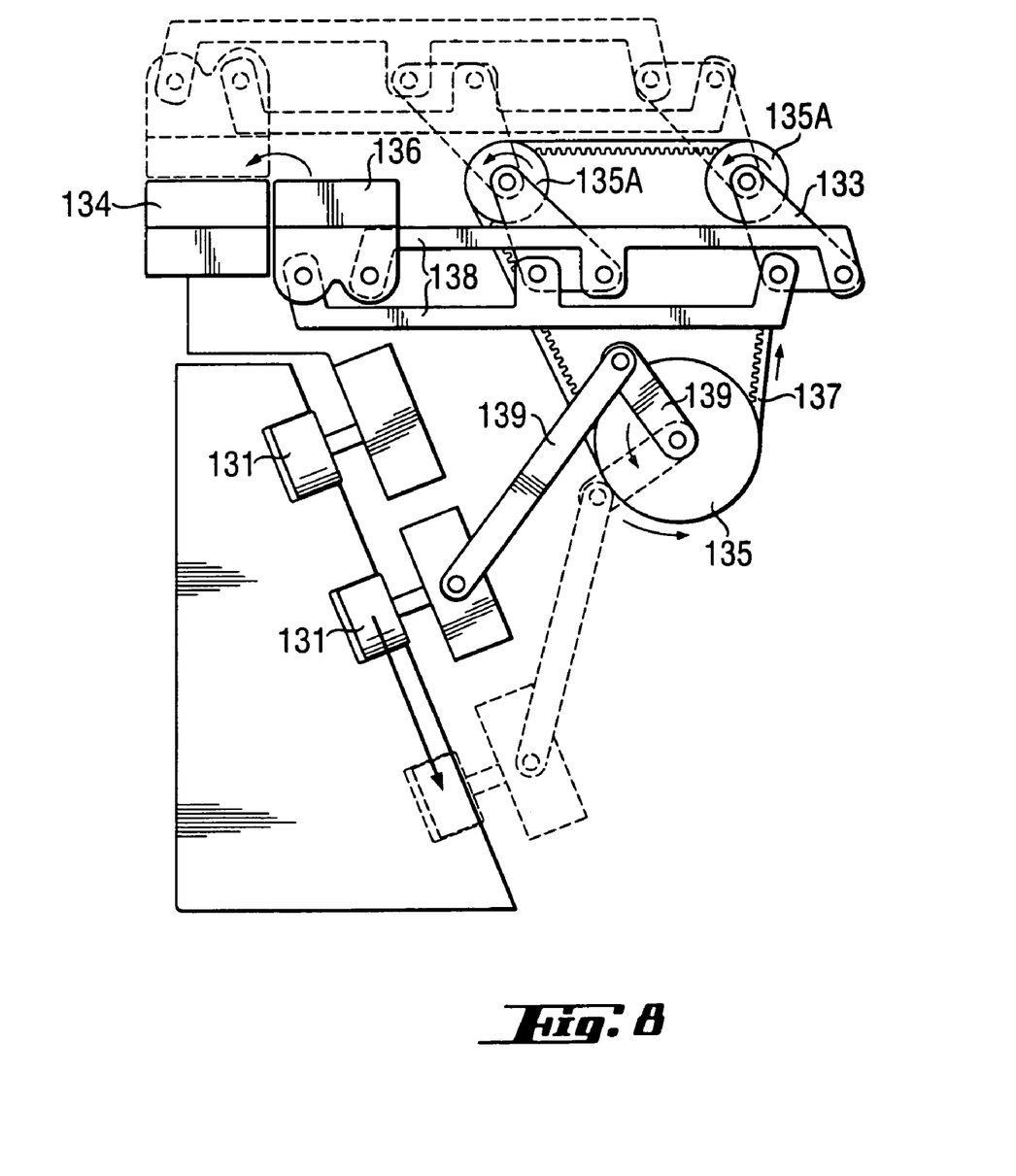
FIG. 8 is a profile schematic representation of an edge seal folder of the present invention.

In another embodiment, each cam follower 131 can follow an independent cam track that has a width only slightly greater than the diameter of its respective cam follower. In this embodiment there would be no need for the cam followers to be biased, such as by spring loading, each cam follower 131 would simply be guided by its own respective cam track to follow a path corresponding to the opposing surfaces of the cam track 220. Such a design is depicted in FIG. 8, where each cam follower is disposed in its own respective cam track. However, in general, regardless of the actual arrangement of cams and followers, the preferred principle of operation is as described hereinbelow.

As shown in FIG. 5, the inner cam track surface 222 and the outer cam track surface 224 follow non-parallel paths in the region designated as a region of increased cam track width 226. In region 226 the distance between the biased cam followers 131 increases to a maximum separation, and, following the cam track 220 in a counterclockwise manner, decreases back to a minimum spacing, all in a smooth, uninterrupted manner. The region of increased cam track width 226 facilitates the temporary spreading apart of cam followers 131, which spreading is linked by operative linkage to the folding mechanism of each edge seal folder 132, as detailed below.

Thus, in the rotary cycle of apparatus 100, as rotary portion 300 rotates, each edge seal folder 132 is urged in turn by way of the cam followers 131 to region 226 at which time the edge seal folders 132 are actuated into a folding position for as long as the cam followers remain sufficiently separated. As cam followers 131 are urged closer together by the converging paths of the inner and outer cam track surfaces, the edge seal folders once again return to an unfolded configuration. At this stage in the cycle the edge seal portion 152 has been affixed as edge seal 60 to a longitudinal edge of continuous web 140, and the edge seal folder 132 is now ready to be moved back into a position to again receive edge seal web 150, and the cycle continues in a repeating manner.

In a preferred embodiment, the edge seal folder 132 is configured for relatively high-speed operation. That is, the mechanism of folding preferably permits the fold/unfold cycle to complete in a matter of milli-seconds.

Figure 7:
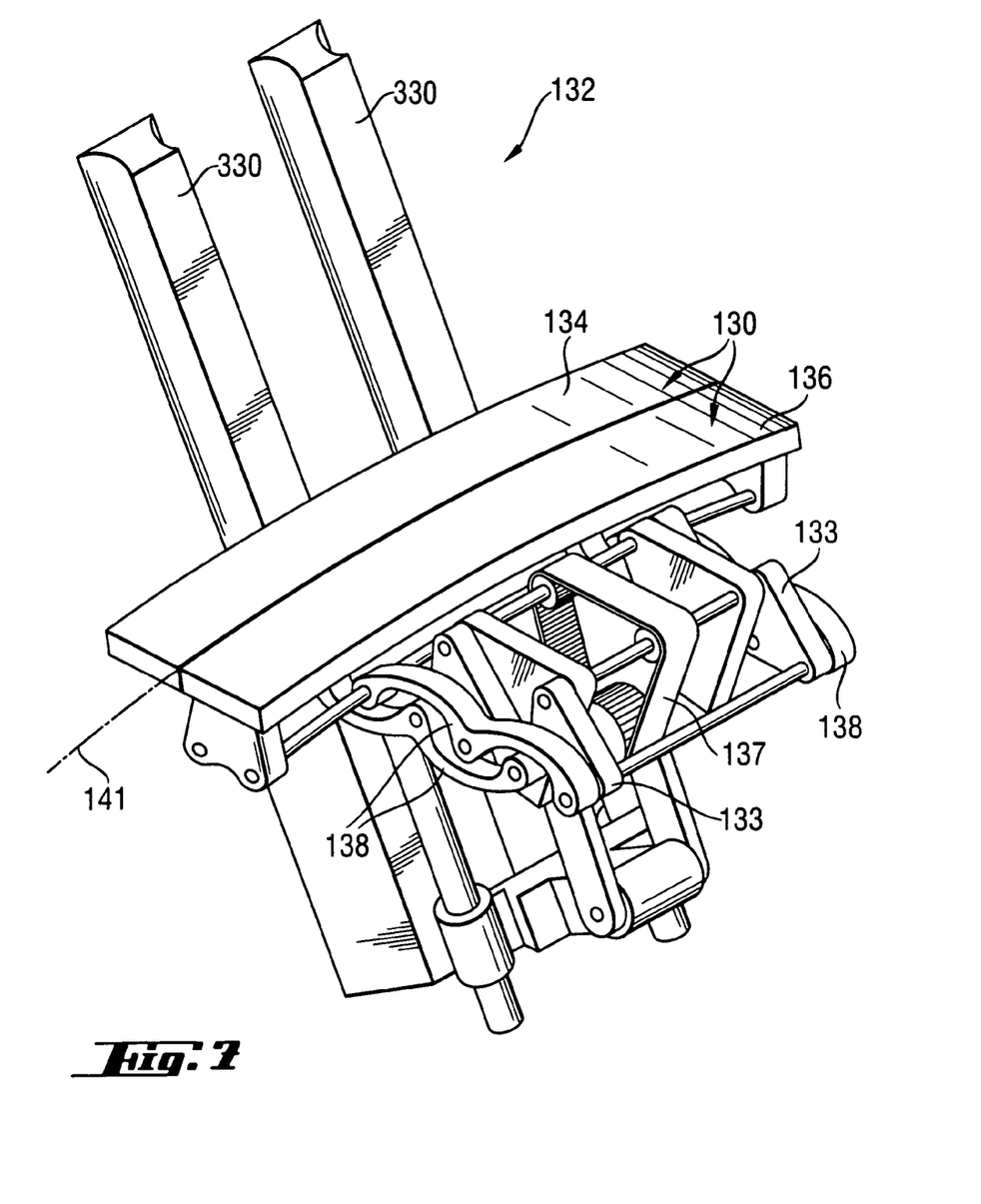
FIG. 7 is a perspective view of one embodiment of an edge seal folder of the present invention.

One configuration found successful in high-speed operation is shown in FIGS. 7 and 8. Each edge seal folder 132 can comprise at least two folding portions, a first folding portion 134 and a second folding portion 136. The edge seal folders 132 can have more than one folding portion, but at least two are necessary to form a C-folded edge seal 60. In operation, second folding portion 136 is rotated about axis 141 to facilitate C-folding of edge seal portion 152 to form edge seal 60.

Because edge seal folder 132 preferably has a curved surface which forms second web surface 130, second folding portion 136 is preferably capable of inverting its curvature upon actuation of the folding operation. That is, before folding, the second web surface 130 of second folding portion 136 preferably forms what can be described as a convex surface. However, after the folding operation the second web surface 130 of second folding portion 136 forms what can be described as a concave surface, which together with the still convex second web surface 130 of first folding portion 134, can apply generally uniform folding pressure along the length of folded edge seal portion 152. Therefore, second folding portion 136 is preferably pliable, bendable, or otherwise deformable to enable repeated bending cycles, such as polyurethane, for example.

When each leg cuff folder 132 is in the web-receiving position, such as 132A in FIG. 4, the first and second folding portions 134, and 136, are "opened" as shown in FIGS. 7 and 8, such that together they define a relatively flat second web surface 130. However, a slight offset of the second web surface 130 of the first and second folding portions 134, and 136 can be beneficial. By "offset" is meant a slight difference in D2min between first and second folding portions 134, and 136 with second folding portion 136 having a slightly greater D2min, such that upon rotation of second folding portion, as described below, a gap is formed between first and second folding portions 134, and 136 in the folded position. This gap can be predetermined and adjusted depending upon the basis weight and/or thickness of the particular web materials 140, 150 utilized. In one embodiment, when in the open, unfolded position, there can be essentially no gap between first and second folding portions 134, and 136, along their adjacent edges.

In the embodiment shown in FIGS. 7 and 8, the first and second folding portions 134, and 136 are separately supported in a side-by-side, adjacent relationship, that is, they are not hinged or otherwise joined to one another. The first and second folding portions 134, and 136 are disposed in an articulating relationship relative to each other, such that one portion can be rotated or "flipped" 180 degrees about axis 141 to achieve the folding of edge seal portion 152 (not shown in FIGS. 7 and 8).

One suitable method of accomplishing high-speed folding of edge seal portion 152 is shown in the schematic representation of FIG. 8. First folding portion 134 is mounted in a non-rotating relationship with respect to edge seal folder 132. Second folding portion 136 is unattached to first folding portion 134 and is supported in a rotatable position by mechanisms operatively linked to cam followers 131. In the embodiment shown, primary linkage 139 is operative attached by suitable pivot arms to one of the cam followers 131, specifically the inner cam follower relative to axis 110. With reference to FIG. 5, it can be seen that the inner cam follower, following the inner cam track surface 222 in the region of increased cam track width 226 moves inwardly with respect to axis 110, thereby initiating the folding motion of edge seal folder 132.

As inner cam follower moves, linkage 139 rotates belt drive 135 to rotate in the direction indicated. Belt drive 135 moves drive belt 137 which thereby turns at least one drive roller 131, which turns an associated linkage connector 133, which itself is operatively connected to linkage 138 which comprises a cooperating pair of links that are configured to facilitate a 180 degree fold over motion of second folding portion 136. Other supporting links, shafts, bearings, and the like, which are not necessarily shown, can be configured in known ways to complete the linkage. Thus, there is direct mechanical linkage between the cam track 220 and the first and second folding portions 134, 136 that permits high-speed, synchronized, folding of edge seal portion 152 to form edge seal 60 of a diaper being processed on apparatus 100. The various components are shown in the folded configuration by the phantom lines of FIG. 8.

In a preferred embodiment, belt drive 135 has a diameter exactly twice the diameter of drive roller(s) 131, such that as belt drive 135 rotates through an arc of 90 degrees, drive roller(s) 131 rotate through 180 degrees.

Once folded about a longitudinal edge of continuous web 140, edge seal portions 152 are joined to continuous web 140 by methods known in the art for assembling components of absorbent articles, particularly disposable absorbent articles. In a preferred embodiment, edge seal portions 152 are affixed by adhesive, such as hot melt adhesive. The adhesive can be applied to the continuous web 140 at locations intended to receive the edge seal portions 152, or adhesive can be applied to one surface of the edge seal web 150 prior to being cut by rotary knife 320. Adhesive can be applied by methods known in the art, including extrusion, spraying, slot coating, or wiping. In one embodiment, adhesive is applied by extruding hot melt adhesive beads from adhesive applicators 350 placed to facilitate adhesive application to edge seal web 150. The particular method and location of applying adhesive depends on the type of adhesive used, and its cure rate, and is not considered critical to the present invention. In one embodiment Findley H2031 adhesive, applied by spraying onto edge seal web 150 was used.

In one embodiment, the edge seal web 150 comprises elastic material, or highly elastic material, and is received onto edge seal folders 132 as a tensioned web of material in an extended state. Once applied to the longitudinal edge of continuous web 140, the edge seal 60 so formed can remain in an extended, stretched configuration. Once continuous web 140 is cut and formed into a diaper, edge seal 60 can relax, contract, and form a soft, gathered, finished cuff about the leg portion of diaper 20. In one embodiment, edge seal web 150 comprises nonwoven material comprising elastomeric strands of an elastomeric polymer, such as Kraton®, Lycra®, or Spandex® strands.

In one embodiment, edge seal web 150 comprises at least one strand of elastomeric polymer strand(s) enveloped in a fold along one longitudinal edge thereof. The width of edge seal web 150, including the edge having enclosed therein an elastomeric strand is adequate to provide not only an edge seal, but also the integrated barrier cuff 61 as shown in FIG. 3. Thus, upon folding, edge seal portion 152, having an extended width, forms not only edge seal 60, but integrated barrier cuff 61.

Figure 9:
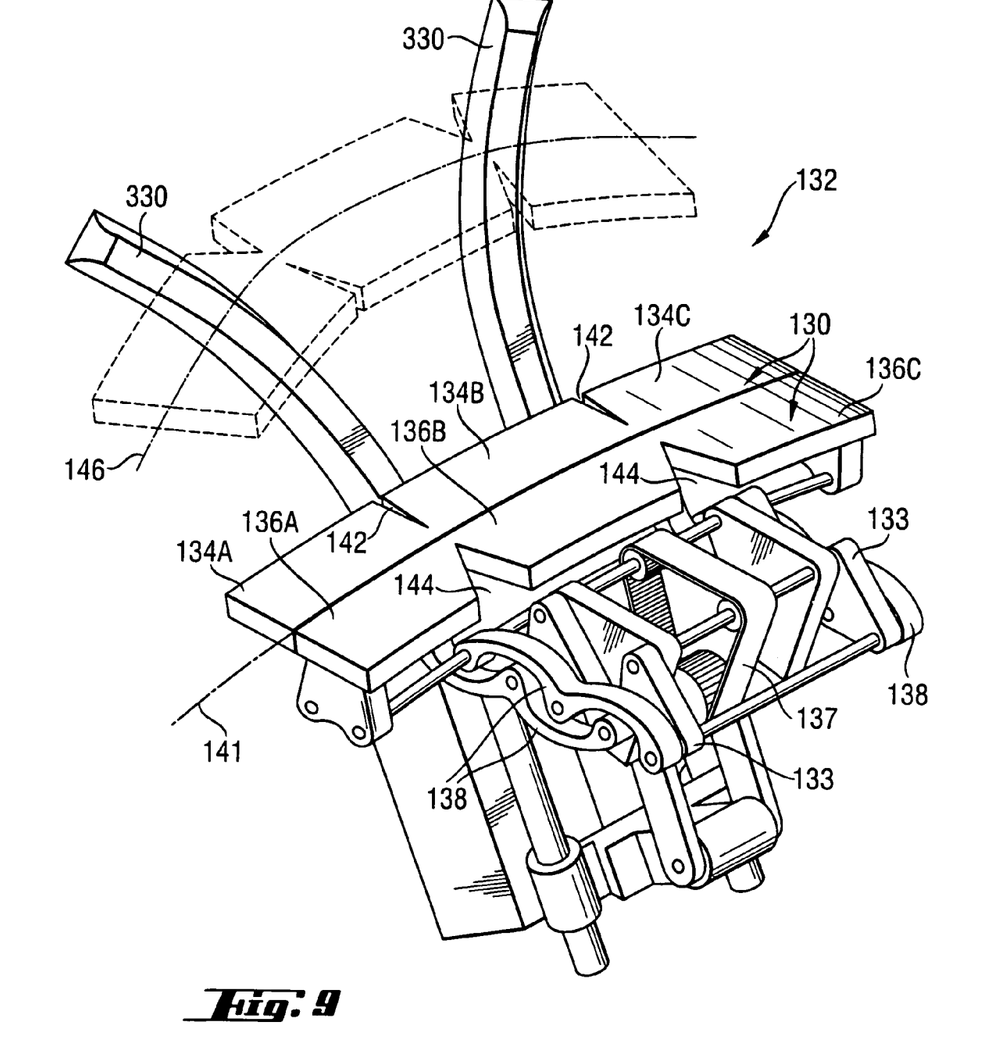
FIG. 9 is a perspective view of an alternative embodiment of an edge seal folder of the present invention.

In a preferred embodiment, edge seals 60 are not straight when applied to the longitudinal edge 50 of diaper 20 (and, therefore, not straight when applied as edge seal portion 152 to a longitudinal edge of continuous web 140). In a preferred embodiment, edge seals 60 follow the contour of the concave-shaped portions of a diaper (in a flat-out condition, as shown in FIG. 1) of a diaper having an "hourglass" shape. Therefore, in a preferred embodiment, because edge seal web 150 is received as a "straight" web, and edge seal segment 152 is therefore received in an "un-curved" configuration, each of first and second folding portions 134, 136 of edge seal folders 132 are segmented such that the segments can articulate with respect to one another. Such articulating segments are shown schematically in FIG. 9. As shown, first and second folding portions 134, 136 each comprise segments, denoted in FIG. 9 as segments A, B, and C. However, in practice, the number of segments can be varied as necessary to achieve the curvature of edge seal 60 desired. The segments can be separated by partial slits 142, and V-shaped openings 144. In this embodiment, guides 330 do not follow a completely linear path, but as edge seal folder 132 nears D2max, guides 330 deviate from linear, for example by twisting with respect to each other. The exact path of guides 330 is difficult to describe in words, but results in at least one or both of segments 134A and 134C articulating with respect to 134B, for example, such that slit 142 opens up in a V shape, and V-shaped opening 144 closes up, so that the interface between first and second folding portions 134, 136 forms a curve, designated 146 in FIG. 9. Therefore, once folded upon the longitudinal edge of continuous web 140, the resulting edge seal 60 can be curved, following the contour of longitudinal edge 50 of the finished article, as shown in FIG. 1.

While particular embodiments of the present invention have been illustrated and described, it would be apparent to those skilled in the art that various other combinations and modifications can be made without departing from the scope of the invention. It is therefore intended to cover in the appended claims all such combinations and modifications that are within the scope of this invention.

What is claimed is:

1. A disposable diaper comprising a topsheet, a backsheet, and an absorbent core disposed between said topsheet and said backsheet, said topsheet and said backsheet defining a periphery and longitudinal edges, portions of said longitudinal edges defining leg openings when said disposable diaper is worn, said disposable diaper comprising on each longitudinal edge a discrete edge seal folded about and joined to said longitudinal edges at least at said portions of said longitudinal edges defining leg openings when said disposable diaper is worn, wherein said discrete edge seal completely encircles said portion of said longitudinal edges defining said leg openings, wherein said discrete edge seals do not extend the entire length of said longitudinal edge of said disposable diaper.

2. The disposable diaper of claim 1 wherein said discrete edge seals are joined about each of said longitudinal edges only at said portions of said longitudinal edges defining leg openings.

3. The disposable diaper of claim 1 wherein said edge discrete seal comprises an elastomeric material.

4. The disposable diaper of claim 1 wherein said discrete edge seal comprises a nonwoven material.

5. The disposable diaper of claim 1, wherein said discrete edge seal comprises at least one elastomerie strand.

6. The disposable diaper of claim 1, wherein said discrete edge seal further comprises a barrier cuff.

7. The disposable diaper of claim 1 wherein said diaper exhibits an hourglass shape having inwardly-curved portions of said longitudinal edges when in a flat-out state.

8. The disposable diaper of claim 7, wherein said discrete edge seal is affixed only at said inwardly-curved portions of said longitudinal edges.

* * * * *

UNITED STATES PATENT AND TRADEMARK OFFICE
CERTIFICATE OF CORRECTION

PATENT NO. : 7,179,248 B2
APPLICATION NO. : 11/312616
DATED : February 20, 2007
INVENTOR(S) : Uwe Schneider et al.

It is certified that error appears in the above-identified patent and that said Letters Patent is hereby corrected as shown below:

<u>Column 18</u>
Line 57, delete "elastomerie" and insert -- elastomeric --.

Signed and Sealed this

Twenty-eighth Day of August, 2007

JON W. DUDAS
*Director of the United States Patent and Trademark Office*